United States Patent
Lee et al.

(10) Patent No.: US 6,894,129 B2
(45) Date of Patent: May 17, 2005

(54) MULTINUCLEAR HALF METALLOCENE CATALYST AND PREPARATION OF STYRENE POLYMER USING THE SAME

(75) Inventors: Min-Hyung Lee, Daejeon (KR); You-Mi Jeong, Daejeon (KR); Jin-Young Ryu, Daejeon (KR)

(73) Assignee: LG Chem, Ltd. (KR)

( * ) Notice: Subject to any disclaimer, the term of this patent is extended or adjusted under 35 U.S.C. 154(b) by 81 days.

(21) Appl. No.: 10/380,022
(22) PCT Filed: Jul. 11, 2002
(86) PCT No.: PCT/KR02/01317
§ 371 (c)(1), (2), (4) Date: Mar. 6, 2003
(87) PCT Pub. No.: WO03/006473
PCT Pub. Date: Jan. 23, 2003

(65) Prior Publication Data
US 2004/0048737 A1 Mar. 11, 2004

(30) Foreign Application Priority Data
Jul. 11, 2001 (KR) ......................................... 2001-41580

(51) Int. Cl.⁷ .............................. C08F 4/60; C08F 4/64; C08F 4/642; C08F 112/08
(52) U.S. Cl. ........................ 526/114; 526/160; 526/161; 526/172; 526/346; 526/347; 526/347.1; 502/103; 502/117; 502/152; 502/155; 556/52; 556/55; 556/1
(58) Field of Search .................................. 526/114, 160, 526/161, 172, 346, 347, 347.1; 502/152, 155; 556/52, 55

(56) References Cited

U.S. PATENT DOCUMENTS

| 6,010,972 A | 1/2000 | Zacharias et al. |
| 6,010,974 A | 1/2000 | Kim et al. |
| 6,235,917 B1 | 5/2001 | Graf et al. |

FOREIGN PATENT DOCUMENTS

| CA | 2026552 | 3/1991 |
| EP | 0 210 615 | 11/1990 |
| EP | 0 964 004 | 12/1999 |
| EP | 0 985 676 | 3/2000 |
| JP | 4314790 | 11/1992 |
| WO | WO 00/52063 | 9/2000 |
| WO | WO 00/78827 | 12/2000 |

OTHER PUBLICATIONS

Y. Kim, et al., "New half–sandwich metallocene catalyst for polyethylene and polystyrene", Journal of Organometallic Chemistry 634, 2001, pp. 19–24.

Y. Tianger, et al., "Recent Advances in Synthesis of Novel Half–Sandwich Group 4 Metallocene Complexes", Chemical Journal on Internet, retrieved on Aug. 29, 2002.

Y. Kim, et al., New Half–Metallocene Catalysts Generating Polyethylene with Bimodal Molecular Weight Distribution and Syndiotactic Polystyrene, Macromol Rapid Commun., 22, 2001, pp. 573–578.

International Search Report; PCT/KR02/01317; Oct., 9, 2002.

*Primary Examiner*—Roberto Rabago
(74) *Attorney, Agent, or Firm*—Cantor Colburn LLP

(57) ABSTRACT

The present invention relates to a catalyst for preparing vinyl aromatic polymer and styrene polymerization using the same, and particularly to a transition metal half metallocene catalyst with a novel structure for preparing syndiotactic styrene polymer having high activity, superior stereoregularity, high melting point and various molecular weight distributions and a process for preparing styrene polymer using the same. The present invention provides a multinuclear half metallocene compound in which two or more of transition metals of groups 3 to 10 on periodic table are connected through bridge ligand simultaneously containing $\pi$-ligand cycloalkandienyl group and $\sigma$-ligand functional group and its preparation, and a process for preparing styrene polymer using the compound as a catalyst. Polymers with various molecular weight distributions as well as vinyl aromatic polymer having predominant syndiotactic structure can be prepared with high activity using the multinuclear half metallocene catalyst.

4 Claims, No Drawings

MULTINUCLEAR HALF METALLOCENE CATALYST AND PREPARATION OF STYRENE POLYMER USING THE SAME

BACKGROUND OF THE INVENTION (a) Field of the Invention

The present invention relates to a catalyst for preparing vinyl aromatic polymer and polymerization process of styrene using the same, and particularly to a transition metal half metallocene catalyst with a novel structure for preparing syndiotactic styrene polymer having high activity, superior stereoregularity, high melting point and various molecular weight distributions and a process for preparing polymer using the same.

(b) Description of the Related Art

Styrene polymer is largely classified into three kinds of polymers of atactic, isotactic and syndiotactic polystyrene according to arrangement of benzene ring attached to a polymer main chain.

Amorphous atactic polystyrene is a thermoplastic polymer obtained by general radical or ion polymerization. It is prepared by various processing methods such as injection molding, extrusion molding or vacuum forming, etc. and is used for packaging material, housing material for daily commodities, toy, electrical and electronic products, etc. Isotactic polystyrene having stereoregularity is mainly obtained using heterogeneous Ziegler-Natta catalyst but it is not widely used due to low productivity and low crystallization speed.

Meanwhile, syndiotactic polystyrene is used for engineering plastics more than general-purpose resin because it has properties of crystalline polymer due to high stereoregularity, i.e., heat resistance and chemical resistance, and good mechanical properties such as high crystallization speed while maintaining processing forming property and electrical property of general amorphous polystyrene. Therefore, syndiotactic polystyrene is suitable for material for electronic parts or automobile engine parts, and is used for parts of cellular phone or microwave oven using high frequency property.

Such syndiotactic polystyrene can be generally prepared using a 4 group transition metal compound metallocene catalyst with π-ligand and σ-ligand. As the π-ligand, cyclopentadienyl, indenyl, fluorenyl group or derivatives thereof can be used, and as the σ-ligand, alkyl, aryl, alkyl, alkoxy, aryloxy, thioalkoxy, thioaryloxy, amino, amido, carboxyl, alkyl sillyl group, halogen, etc. can be used.

EP 210,615 has disclosed a method for synthesizing syndiotactic polystyrene with high yield by combining metallocene catalyst with the above structure as a main catalyst with alkylaluminoxane as a cocatalyst. More particularly, main catalyst such as cyclopentadienyltitanium trichloride or pentamethylcyclopentadienyltitanium trichloride is activated with methylaluminoxane cocatalyst and used for polymerization of syndiotactic polystyrene with superior stereoregularity.

Japanese Laid-Open Patent Publication No. Hei 4-314, 790 has described that when chloro group, coligand of a metallocene catalyst with the above-mentioned structure, is substituted with alkoxy group, specifically when pentamethylcyclopentadienyltitanium trimethoxide main catalyst and methylaluminoxane cocatalyst are used, syndiotactic polystyrene can be obtained with much higher yield.

Canadian Laid-Open Patent Publication No. CA 2,026, 552 has disclosed a method for preparing syndiotactic polystyrene having broad molecular weight distribution by using two or more kinds of the metallocene catalysts together in polymerization. It is to diversify narrow molecular weight distribution obtained when only one kind of a catalyst exists. However, in such a case, since introduced catalysts independently participate in polymerization, produced polystyrenes are also independent each other and thus they are difficult to be uniformly mixed in molecular unit.

U.S. Pat. No. 6,010,972 has disclosed preparation of di-nuclear half metallocene catalyst in which two cycloalkandienyl groups are connected to both nuclei through alkylene or sillylene bridge and styrene polymerization using the same. The result of styrene polymerization showed high polymerization activity, superior stereoregularity and narrow molecular weight distribution similarly to mononuclear metallocene, indicating that even if two or more metal centers exist in one molecule, they do not hinder a polymerization. However, since both cycloalkandienyl groups are the same due to the used preparation process of main ligand, it is not effective for providing various polystyrenes, one of advantages of multinuclear metallocene catalyst, as can be seen from narrow molecular weight distribution.

EP 964,004 has disclosed preparation of multinuclear metallocene catalyst in which two or more half metallocenes are connected through coligand bridge having dialkoxy group or diaryloxy group and styrene polymerization using the same. The results of styrene polymerization also showed high polymerization activity, superior stereoregularity and narrow molecular weight distribution. However, since the used coligand has symmetric structure and acts as a leaving group when polymerization, produced polystyrenes show little difference from those produced using mononuclear metallocene catalyst.

SUMMARY OF THE INVENTION

The present invention is made in consideration of the problems of the prior art, and it is an object of the present invention to provide a novel multinuclear metallocene catalyst capable of preparing syndiotactic polystyrene having high stereoregularity and various molecular weight distributions with high activity, and homopolymerization of styrene and copolymerization of styrene and olefin using the same.

It is another object of the present invention to provide a multinuclear half metallocene catalyst comprising at least two transition metal compounds of Group 3 to 10 in periodic table and having cycloalkandienyl group.

It is another object of the present invention to provide a process for preparing a multinuclear half metallocene catalyst using a bridge ligand simultaneously comprising π-ligand cycloalkandienyl group and σ-ligand functional group.

It is another object of the present invention to provide a process for preparing syndiotactic polystyrene having superior stereoregularity, high melting temperature and various molecular weight distributions, and styrene polymers such as copolymer with olefin in high yield using the metallocene catalyst.

In order to achieve these objects, the present invention provides a multinuclear half metallocene catalyst represented by the following Chemical Formula 1, 2 or 3:

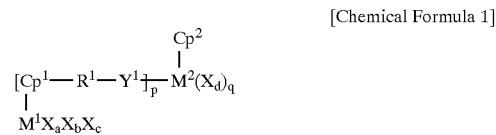

[Chemical Formula 1]

-continued

[Chemical Formula 2]

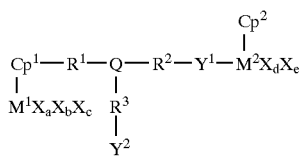

[Chemical Formula 3]

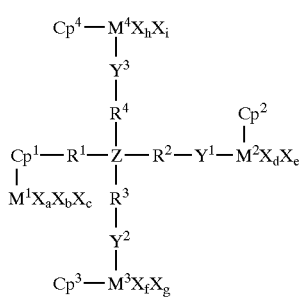

In the Chemical Formulae 1, 2 and 3, $M^1$, $M^2$, $M^3$ and $M^4$ are, independently or simultaneously in the same formula, transition atoms of group 3 to 10 in periodic table;

$Cp^1$, $Cp^2$, $Cp^3$ and $Cp^4$ are, independently or simultaneously in the same formula, cycloalkandienyl ligand represented by the following Chemical Formula 4, 5, 6, 7 or 8:

[Chemical Formula 4]

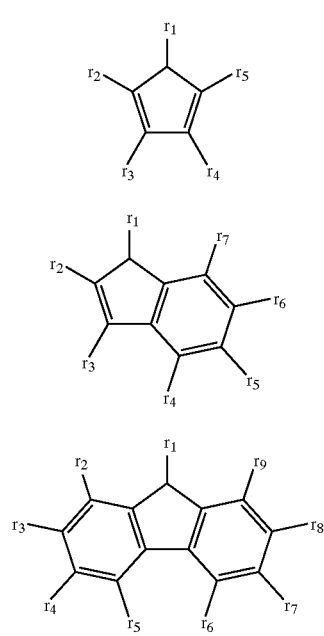

[Chemical Formula 5]

[Chemical Formula 6]

[Chemical Formula 7]

[Chemical Formula 8]

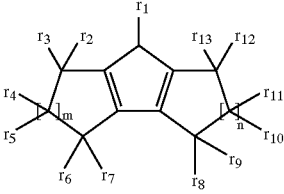

(In the Chemical Formulae 4, 5, 6, 7 and 8, $r^1$, $r^2$, $r^3$, $r^4$, $r^5$, $r^6$, $r^7$, $r^8$, $r^9$, $r^{10}$, $r^{11}$, $r^{12}$ and $r^{13}$ are, independently or simultaneously in the same formula, a hydrogen atom, halogen, C1–20 alkyl, cycloalkyl, alkenyl, alkylsillyl, haloalkyl, alkoxy, alkylsiloxy, amino, alkoxyalkyl, thioalkoxyalkyl, alkylsilloxyalkyl, aminoalkyl, alkylphosphinoalkyl, C6–40 aryl, arylalkyl, alkylaryl, arylsillyl, arylalkylsillyl, haloaryl, aryloxy, aryloxoalkyl, thioaryloxoalkyl, aryloxoaryl, arylsilloxy, arylalkylsilloxy, arylsilloxoalkyl, arylsilloxoaryl, arylamino, arylaminoalkyl, arylaminoaryl or arylphosphinoalkyl group, and each of m and n is an integer of 1 or more);

$X_a$, $X_b$, $X_c$, $X_d$, $X_e$, $X_f$, $X_g$, $X_h$ and $X_i$ are σ-ligand functional groups, and independently or simultaneously in the same formula, a hydrogen atom halogen, hydroxy, C1–20 alkyl, cycloalkyl, alkylsillyl, alkenyl, alkoxy, alkenyloxy, thioalkoxy, alkylsilloxy, amide, alkoxyalcohol, alcoholamine, carboxyl, sulfonyl, C6–40 aryl, alkylaryl, arylalkyl, arylsillyl, haloaryl, aryloxy, arylalkoxy, thioaryloxy, arylsilloxy, arylalkylsilloxy, arylamide, arylalkylamide, aryloxoalcohol, alcoholarylamine or aryl aminoaryloxy group;

$R^1$, $R^2$, $R^3$ and $R^4$ are bridges connecting the transition metal $M^1$, $M^2$, $M^3$ or $M^4$ with the cycloalkandienyl ligand $Cp^1$, $Cp^2$, $Cp^3$ or $Cp^4$, and independently or simultaneously in the same formula, C1–20 alkyl, cycloalkyl, alkenyl, alkylsillyl, haloalkyl, alkoxy, alkylsilloxy, amino, dialkylether, dialkylthioether, alkylsilloxyalkyl, alkylaminoalkyl, alkylphosphinoalkyl, C6–40 aryl, arylalkyl, alkylaryl, arylsillyl, arylalkylsillyl, haloaryl, aryloxy, aryloxoalkyl, thioaryloxoalkyl, aryloxoaryl, arylsilloxy, arylalkylsilloxy, arylsilloxoalkyl, arylsilloxoaryl, arylamino, arylaminoalkyl, arylaminoaryl or arylphosphinoalkyl group;

Z is a carbon, silicon or germanium,

Q is a nitrogen, phosphorous, C-$r_{14}$, Si-$r_{15}$ or Ge-$r_{16}$, $Y^1$, $Y^2$ and $Y^3$ are σ-ligand functional groups, and independently or simultaneously in the same formula, oxygen, sulfur, carboxyl, sulfonyl group, N-$r_{17}$ or P-$r_{18}$;

In the C-$r_{14}$, Si-$r_{15}$, Ge-$r_{16}$, N-$r_{17}$ and P-$r_{18}$, each of $r_{14}$, $r_{15}$, $r_{16}$, $r_{17}$ and $r_{18}$ is selected from a group consisting of hydrogen, halogen, C1–20 alkyl, cycloalkyl, alkenyl, alkylsillyl, haloalkyl, alkoxy, alkylsilloxy, amino, alkoxyalkyl, thioalkoxyalkyl, alkylsilloxyalkyl, aminoalkyl, alkylphosphinoalkyl, aryl, arylalkyl, alkylaryl, arylsillyl, arylalkylsillyl, haloaryl, aryloxy, aryloxoalkyl, thioaryloxoalkyl, aryloxoaryl, arylsilloxy, arylalkylsilloxy, arylsilloxoalkyl, arylsilloxoaryl, arylamino, arylaminoalkyl, arylaminoaryl and arylphosphinoalkyl;

p is an integer of 1 to 3, and q is an integer of 0 to 2, and p+q=3.

The present invention also provides a process for preparing styrene polymer comprising the step of polymerizing styrene monomers in the presence of a catalyst system comprising a) a multinuclear half metallocene compound catalyst represented by the above Chemical Formula 1, 2 or 3, and b) a cocatalyst selected from a group consisting of
i) alkylaluminoxane;
ii) a mixture of alkylaluminoxane and alkylaluminum; and
iii) a mixture of week coordinate Lewis acid and alkylaluminum.

DETAILED DESCRIPTION AND THE PREFERRED EMBODIMENTS

The present invention will now be explained in detail.

The present invention provides a multinuclear half metallocene catalyst satisfying the above Chemical Formula 1, 2 or 3 as a main catalyst used for preparing styrene polymer and preparation thereof, and a process for preparing styrene polymer using the catalyst as a main catalyst.

The metallocene catalyst of the present invention satisfying the above Chemical Formula 1, 2 or 3 is a multinuclear half metallocene compound in which two or more transition metals of group 3 to 10 in periodic table are connected through a bridge simultaneously containing cycloalkandienyl group and one or more functional groups. Therefore, each metal center makes different cationic polymerization active kinds and thus polymers with various molecular weights are uniformly mixed in molecular unit, making molecular weight control of polymers easy, as well as providing styrene polymer having high polymerization activity, superior stereoregularity and high melting temperature, which is advantages of the existing mononuclear metallocene. Therefore, difficulty in processibility of polymer due to narrow molecular weight distribution, which is a disadvantage of the metallocene catalyst, can be overcome and polymers with various physical properties can be provided.

The multinuclear half metallocene catalyst can be prepared by reacting a ligand simultaneously containing cycloalkandienyl group and at least one functional groups with a half metallocene compound having a leaving group to introduce functional group of the ligand into a transition metal, and i) converting the cycloalkandienyl group into an alkali metal salt thereof and reacting it with another transition metal compound having a leaving group, or ii) introducing alkylsillyl group or alkyl tin group into the cycloalkandienyl group and reacting it with a transition metal compound.

In addition, the ligand simultaneously containing cycloalkandienyl group and at least one functional groups can be prepared by i) reacting an alkali metal salt of a cycloalkandienyl group with an organic compound simultaneously containing a leaving group and a functional group, or ii) reacting an alkali metal salt of an organic compound containing a functional group with a ketone compound having cycloalkandienyl backbone.

The alkali metal salt of cycloalkandienyl group includes cyclopentadienyl lithium, cyclopentadienyl sodium, cyclopentadienyl potassium, cyclopentadienyl magnesium, methylcyclopentadienyl lithium, methylcyclopentadienyl sodium, methylcyclopentadienyl potassium, tetramethylcyclopentadienyl lithium, tetramethylcyclopentadienyl sodium, tetramethylcyclopentadienyl potassium, indenyl lithium, indenyl sodium, indenyl potassium, fluorenyl lithium, etc. These salts can be prepared by reacting a ligand having a cycloalkandienyl structure with n-butyllithium, s-butyllithium, t-butyllithium, methyllithium, sodium methoxide, sodium ethoxide, potassium t-butoxide, potassium hydroxide, methylmagnesium chloride, ethylmagnesium bromide, dimethylmagnesium, lithium, sodium, potassium, etc.

In addition, the organic compound simultaneously containing a leaving group and a functional group includes 2-bromo-1-ethanol, 4-bromo-1-butanol, 5-bromo-1-pentanol, 6-bromo-1-hexanol, 9-bromo-1-nonanol, 10-bromo-1-decanol, 4-hydroxybenzylbromide, (2-bromoethyl)-methyl-N-ethanolamine, (2-bromoethyl)-N,N-diethanolamine 4-bromophenol, 4-bromo-2,6-dimethylphenol, 4-(4-bromophenyl)phenol, 4-bromobenzylalcohol, 4-bromoaniline, 4-bromobenzylamine, 4-bromobutyric acid, 6-bromohexyl, 4-bromo benzoic acid, etc.

The ketone compound capable of having cycloalkandienyl backbone includes 2-cyclopentene-1-one, 3-methyl-2-cyclopentene-1-one, 3,4-dimethyl2-cyclopenten-1-one, 2,3,4-trimethyl-2-cyclopenten-1-one, 2,3,4,5-tetramethyl-2-cyclopenten-1-one, 3-ethyl-2-cyclopenten-1-one, 3-t-butyl-2-cyclopenten-1-one, 3,4-diphenyl-2-cyclopenten-1-one, 1-indanone, 2-indanone, 4,5,6,7-tetrahydro-1-indanone, 4,5,6,7-tetrahydro-2-indanone, etc.

The half metallocene compound having a leaving group includes cyclopentadienyltitanium trichloride, cyclopentadienylmethoxytitanium dichloride, cyclopentadienylmethoxytitanium monochloride, cyclopentadienyltitanium trimethoxide, methylcyclopentadienyltitanium trichloride, methylcyclopentadienylmethoxytitaium dichloride, methylcyclopentadienylmethoxytitaium monochloride, methylcyclopentadienyltitanium trimethoxide, pentamethylcyclopentadienyltitanium trichloride, pentamethylcyclopentadienylmethoxytitanium dichloride, pentamethylcyclopentadienylmethoxytitanium monochloride, pentamethylcyclopentadienyltitanium trimethoxide, indenyltitanium trichloride, indenylmethoxytitanium dichloride, indenyldimethoxytitanium monochloride, indenyltitanium dichloride, indenyldimethoxytitanium monochloride, indenyltitanium trimethoxide, etc.

The transition metal compound having a leaving group includes titanium tetrachloride, titanium tetrachloride ditetrahydrofuran, zirconium tetrachloride, hafnium tetrachloride, vanadium tetrachloride, titanium tetraiodide titanium tetrabromide, titanium tetrafluoride, vanadium chloride oxide, titanium tetraisopropoxide, chlorotitanium triisopropoxide, dichlorotitanium diisoproxide, trichlorotitanium monoisopropoxide, chlorotitanium triphenoxide, chlorotitanium tributoxide, chlorotitanium triethoxide, etc.

The alkylsillyl group or alkyl tin group that can be substituted for the cycloalkandienyl group includes trimethylsillyl, triethylsillyl, butyldimethylsillyl, phenyldimethylsillyl, trimethyl tin, triethyl tin, tributyl tin, etc.

In the multinuclear half metallocene catalyst for preparing styrene polymer, represented by the above Chemical Formula 1, 2 or 3, prepared by the above process, n and m preferably satisfy $1 \leq n$ or $m \leq 10$.

And, $M^1$ to $M^4$ are preferably group 4 transition metal on periodic table, and more preferably titanium, zirconium or hafnium.

And, the ligand having cycloalkandienyl backbone includes cyclopentadienyl group, indenyl group, fluorenyl group, 4,5,6,7-tetrahydroindenyl group, 2,3,4,5,6,7,8,9-octahydrofluorenyl group, etc.

The C1–20 alkyl, cycloalkyl, alkenyl, alkylsillyl, haloalkyl, alkoxy, alkylsilloxy, amino, alkoxyalkyl, thioalkoxyalkyl, alkylsilloxyalkyl, aminoalkyl, alkylphosphinoalkyl group include methyl, ethyl, propyl, butyl, pentyl, hexyl, cyclopropyl, cyclobutyl, cyclopentyl, cyclohexyl, allyl, 2-butenyl, 2-pentenyl, methylsillyl, dimethylsillyl, trimethylsillyl, ethylsillyl, dietylsillyl, triethylsillyl, propylsillyl, dipropylsillyl, tripropylsillyl, butylsillyl, di-butylsillyl, tri-butylsillyl, butyldimethylsillyl, trifluoromethyl, methoxy, ethoxy, propoxy, butoxy, pentoxy, hexyloxy, methylsilloxy, dimethylsilloxy, trimethylsilloxy, ethylsilloxy, dietylsilloxy, triethylsilloxy, butyldimethylsilloxy, dimethylamino, diethylamino, dipropylamino, dibutylamino, pyrrolidine, piperidine, methoxyethyl, methoxypropyl, methoxybutyl, thiomethoxyethyl, thiomethoxybutyl, trimethylsilloxyethyl, dimethylaminoethyl, diethylphosphinobutyl group, etc.

And, the C6–40 aryl, arylalkyl, alkylaryl, arylsillyl, arylalkylsillyl, haloaryl, aryloxy, aryloxoalkyl, thioaryloxoalkyl, aryloxoaryl, arylsilloxy, arylalkylsilloxy, arylsilloxoalkyl, arylsilloxoaryl, arylamino, arylaminoalkyl, arylaminoaryl, arylphosphinoalkyl group include phenyl, biphenyl, terphenyl, naphtyl, fluorenyl, benzyl, phenylethyl, phenylpropyl, tollyl, xylyl, butylphenyl, phenylsillyl, phenyldimethylsillyl, diphenylmethylsillyl, triphenylsillyl, chlorophenyl, pentafluorophenyl, phenoxy, naphthoxy, phenoxyethyl, biphenoxybutyl, thiophenoxyethyl, phenoxyphenyl, naphthoxyphenyl, phenylsilloxy, triphenylsillyl phenyldimethylsilloxy, triphenylsilloxethyl, diphenylsilloxphenyl, aniline, toluidine, benzylamino, phenylaminoethyl, phenylmethylaminophenyl, diethylphosphinobutyl, etc.

Syndiotactic styrene polymer and styrene copolymer with various physical properties can be obtained using the multinuclear half metallocene catalyst for preparing styrene polymers represented by the above Chemical Formula 1, 2 or 3 as a main catalyst together with a cocatalyst in a styrene homopolymerization or copolymerization with olefin.

The cocatalyst used together with the multinuclear half metallocene catalyst includes alkylaluminoxane of the following Chemical Formula 9 and week coordinate Lewis acid, and they are used together with alkylaluminum of the Chemical Formula 10.

[Chemical Formula 9]

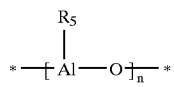

In the Chemical Formula 9, $R_5$ is hydrogen, substituted or unsubstituted C1–20 alkyl, substituted or unsubstituted C3–20 cycloalkyl, C6–40 aryl, alkylaryl or arylalkyl group, and n is an integer of 1 to 100.

[Chemical Formula 10]

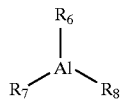

In the Chemical Formula 10, $R_6$, $R_7$ and $R_8$ are independently or simultaneously hydrogen, halogen, substituted or unsubstituted C1–20 alkyl, substituted or unsubstituted C3–20 cycloalkyl, C6–40 aryl, alkylaryl or arylalkyl group; and at least one of the $R_6$, $R_7$ and $R_8$ contain an alkyl group.

The compound of the above Chemical Formula 9 may be linear, circular or network structure, and specifically, the examples include methylaluminoxane, modified methylaluminoxane, ethylaluminoxane, butylaluminoxane, hexylaluminoxane, decylaluminoxane, etc.

The compound of the above Chemical Formula 10 includes trimethylaluminum, dimethylaluminum chloride, dimethylaluminum methoxide, methylaluminum dichloride, triethylaluminum, diethylaluminum chloride, diethylaluminum methoxide, ethylaluminum dichloride, tri-n-propylaluminum, di-n-propylaluminum chloride, n-propylaluminum chloride, triisopropylaluminum, tri-n-butylaluminum, tri-isobutylaluminum, di-isobutylaluminum hydride, etc.

And the weak coordinate Lewis acid cocatalyst may be ionic or neutral type, and specifically, the examples include trimethylammonium, tetraphenylborate, tributylammonium, tetraphenylborate, trimethylammonium tetrakis (pentafluorophenyl)borate, tetramethylammonium tetrakis (pentafluorophenyl)borate, N,N-dimethylanilinium tetraphenylborate, dimethylanilinium tetrakis (pentafluorophenyl)borate, pyridinium tetraphenylborate, pyridinium tetrakis(pentafluorophenyl)borate, silver tetrakis (pentafluorophenyl)borate, ferro-cerium tetrakis (pentafluoropehnyl)borate, triphenylcarbenium tetrakis(3,5-bis(trifluoromethyl)phenyl)borate, sodium tetrakis(3,5-bis (trifluoromethyl)phenyl)borate, tris(pentafluorophenyl) borane, tris(2,3,4,5-tetrafluorophenyl)borane, tris(3,5-bis (trifluoromethyl)phenyl)borane, tris(2,4,6-trifluorophenyl) borane, etc.

In styrene polymerization or copolymerization with olefin using the metallocene catalyst, the amount of the cocatalyst used together is not specifically limited but may differ according to the kinds.

The mole ratio of alkylaluminoxane and metallocene catalyst is 1:1 to $10^6$:1, and preferably 10:1 to $10^4$:1. And, the mole ratio of alkylaluminum that can be used together with alkylaluminoxane and metallocene catalyst is 1:1 to $10^4$:1.

The mole ratio of week coordinate Lewis acid and metallocene catalyst is 0.1:1 to 50:1, and the mole ratio of alkylaluminum and metallocene catalyst is 1:1 to 3000:1, and preferably 50:1 to 1000:1.

Monomers that can be polymerized with the catalyst system of the present invention include styrene or its derivatives or olefin, and styrene or its derivatives can be homopolymerized, or styrene and its derivatives can be copolymerized, or styrene or its derivatives can be copolymerized with olefin.

Styrene derivatives have substituents on a benzene ring, and the substituents include halogen, C1–10 alkyl, alkoxy, ester, thioalkoxy, sillyl, tin, amine, phosphine, halogenated alkyl, C2–20 vinyl, aryl, vinylaryl, alkylaryl, aryl alkyl group, etc. Examples include chlorostyrene, bromostyrene, fluorostyrene, p-methylstyrene, m-methylstyrene, ethylstyrene, n-butylstyrene, p-t-butylstyrene, dimethylstyrene, methoxystyrene, ethoxystyrene, butoxystyrene, methyl-4-styrenylester, thiomethoxystyrene, trimethylsillylstyrene, triethylsillylstyrene, t-butyldimethylsillylstyrene, trimethyltin styrene, dimethylaminostyrene, trimethylphosphinostyrene, chloromethylstyrene, bromomethylstyrene, 4-vinylbiphenyl, p-divinylbenzene, m-divinylbenzene, trivinylbenzene, 4,4'-divinylbiphenyl, vinylnaphthalene, etc.

And, the olefins that can be used in copolymerization include C2–20 olefin, C3–20 cycloolefin or cyclodiolefin, C4–20 diolefin, etc., and examples include ethylene, propylene, 1-butene, 1-pentene, 1-hexene, 1-octene, 1decene, cyclopentene, cyclohexene, cyclopentadiene, cyclohexadiene, norbonene, methyl-2-norbonene, 1,3-butadiene, 1,4-pentadiene, 2-methyl-1,3-butadiene, 1,5-hexadiene, etc.

Polymerization using the catalyst system of the present invention can be conducted in a slurry phase, liquid phase, gas phase or massive phase. When a polymerization is conducted in a slurry phase or liquid phase, solvent can be used as a polymerization medium, and the used solvents include C4–20 alkane or cycloalkane solvent such as butane, pentane, hexane, heptane, octane, decane, dodecane, cyclopentane, methylcyclopentane, cyclohexane, etc.;

C6–20 aromatic arene solvent such as benzene, toluene, xylene, mesitylene, etc.; and C1–20 halogen alkane or halogen arene solvent such as dichloromethane, chloromethane, chloroform, carbon tetrachloride, chloroethane, 1,2-dichloroethane, 1,1,2,2-tetrachloroethane, chlorobenzene, 1,2-dichlorobenzene, 1,2,4-trichlorobenzene, etc.

Polymerization temperature is −80 to 200° C., and preferably 0 to 150° C., and polymerization pressure is suitably 1 to 1000 atm including the pressure of comonomers for styrene homopolymerization or copolymerization with olefin.

According to the present invention, polymer can be prepared by i) introducing a solvent and monomers or monomers only into a reactor and elevating a temperature, and then introducing alkylaluminum, cocatalyst and main catalyst metallocene compound in this order, or ii) activating a main catalyst with alkylaluminum and cocatalyst, and then introducing it into a reactor containing monomers, or iii) previously adding alkylaluminum to monomers, and then introducing a main catalyst activated with a cocatalyst. And, the activation by contacting a main catalyst with a cocatalyst is preferably conducted at 0 to 150° C. for 1 to 60 minutes.

The amount of the main catalyst metallocene compound is not specifically limited, but is suitably $10^{-8}$ to 1.0 M on the basis of concentration of central metal in reaction system, and ideally $10^{-7}$ to $10^{-2}$ M.

Syndiotactic styrene polymers and copolymers obtained by polymerization using the catalyst system can be controlled in a molecular weight range of 1000 to 10,000,000 and in a molecular weight distribution range of 1.1 to 100 by controlling the kinds and the amounts of a main catalyst and cocatalyst, reaction temperature, reaction pressure and concentration of monomers.

The present invention will be explained in more detailed with reference to the following Examples. However, these are to illustrate the present invention and the present invention is not limited to them.

EXAMPLE

Example 1

Synthesis of $(O^iPr)_3Ti[Cp(CH_2)_6O]TiCp*(OMe)_2$ (Preparation of $(C_5H_4)(CH_2)_6OH$)

To a 250 ml Schlenk flask containing 1.81 g (10 mmol) of $Br(CH_2)_6OH$, 30 ml of tetrahydrofuran (THF) were added to dissolve, and temperature of a reaction vessel was lowered to −78° C. using dry ice/acetone mixed refrigerant. Then, 1.2 equivalents of NaCp in THF solution were slowly injected using a syringe. After agitating reaction solution at this temperature for 30 minutes, temperature was slowly elevated to maintain a room temperature. The reaction solution was agitated overnight to obtain a light purple solution.

To the reaction mixture, 30 ml of $NH_4Cl$ saturated aqueous solution were poured to terminate a reaction, and then organic solution was extracted twice with 50 ml of diethyl ether. Obtained organic solution was treated with anhydrous magnesium sulfate ($MgSO_4$) to remove moisture, and solution was filtered and then solvent was removed in a rotary evaporator. The solution was dried under vacuum to obtain 1.41 g of $(C_5H_4)(CH_2)_6OH$ (yield 85%).

(Preparation of $(C_5H_4)(CH_2)_6OTiCp*(OMe)_2$)

0.831 g (5 mmol) of the obtained $(C_5H_4)(CH_2)_6OH$ were dissolved in 30 ml of methylene chloride ($CH_2Cl_2$), and 1.1 equivalent of triethylamine (0.767 ml) were added thereto. Then, temperature of a reaction vessel was lowered to −78° C., and the same equivalent of $Cp*Ti(OMe)_2Cl$ (1.40 g) methylene chloride solution dissolved in another flask were slowly dropped thereto with a cannula. White precipitates were immediately observed.

After elevating a temperature of the reaction mixture to a room temperature, the reaction mixture was agitated overnight to obtain yellow reaction solution. After removing solvent under reduced pressure, obtained orange-yellow products were extracted with 30 ml of n-hexane. The products were filtered through celite 545 filter, and triethylamine hydrogen chloride salt and solvent were separated to obtain clear yellow solution. Solvent was removed again from the solution under vacuum, and the solution was dried for a long time to obtain 1.64 g of orange-yellow products $(C_5H_4)(CH_2)_6OTiCp*(OMe)_2$ (yield 80%).

(Preparation of $(O^iPr)_3Ti[Cp(CH_2)_6O]TiCp*(OMe)_2$ catalyst)

After dissolving 0.821 g (2 mmol) of $(C_5H_4)(CH_2)_6OTiCp*(OMe)_2$ synthesized above in 30 ml of diethyl ether, temperature of a reaction vessel was lowered to −78° C. The same equivalents of n-butyllithium in hexane solution were slowly injected with a syringe. Temperature of the reaction vessel was slowly elevated to a room temperature to confirm that light yellow precipitates were produced. After agitating it overnight, temperature of the reaction vessel was lowered again to −78° C., and the same equivalents of $ClTi(O^iPr)_3$ (0.521 g) diethylether solution dissolved in another flask were slowly dropped thereto with a cannula. After removing refrigerating vessel, temperature of a reaction mixture was slowly elevated to maintain a room temperature. At this temperature, the reaction mixture was reacted for one day.

Solvents were completely removed from the reactant, and the reactant was extracted again with 20 ml of n-hexane. It is filtered through celite 545 filter and LiCl and solution were separated to obtain clear light green solution. Solvent was removed from the solution under vacuum and the solution was dried for a long time to obtain 0.888 g of $(O^iPr)_3Ti[Cp(CH_2)_6O]TiCp*(OMe)_2$ (yield 80%).

Example 2

Synthesis of $(O^iPr)_3Ti[Cp(CH_2)_9O]TiCp*(OMe)_2$ catalyst $(O^iPr)_3Ti[Cp(CH_2)_9O]TiCp*(OMe)_2$ catalyst was prepared by the same method as in Example 1, except that $Br(CH_2)_9OH$ was used instead of $Br(CH_2)_6OH$.

Example 3

Synthesis of $(O^iPr)_3Ti[Cp(CH_2)_{12}O]TiCp*(OMe)_2$ catalyst $(OiPr)_3Ti[Cp(CH_2)_{12}O]TiCp*(OMe)_2$ catalyst was prepared by the same method as in Example 1, except that $Br(CH_2)_{12}OH$ was used instead of $Br(CH_2)_6OH$.

Example 4

Synthesis of $(O^iPr)_3Ti[Cp(C_6H_4)2)]TiCp*(OMe)_2$ catalyst (Preparation of $(C_5H_4)(C_6H_4)_2OH$)

To a 250 ml schlenk flask containing 2.49 g (10 mmol) of 4-$Br(C_6H_4)_2OH$, 30 ml of diethyl ether were added to dissolve, and temperature of a reaction vessel was lowered to −78° C. Then, 2 equivalents of n-butyllithium in hexane solution were slowly injected using a syringe and temperature of a reaction mixture was slowly elevated to a room temperature. The reactant was agitated for 4 hours and temperature of a reaction vessel was lowered to −78° C. again, and then 20 ml of 1 equivalent of 2-cyclopenten-1-one (0.821 g) THF solution previously prepared in another flask were dropped thereto using a cannula. The reaction mixture was agitated at this temperature for 30 minutes, and then temperature was elevated to a room temperature and agitated overnight. To a reaction mixture, 30 ml of ammonium chloride ($NH_4Cl$) saturated aqueous solution were poured to terminate a reaction, and then organic solution part was extracted twice with 50 ml of diethyl ether.

Solvents were completely removed from the obtained organic solution using a rotary evaporator, and obtained oily compound was dissolved in 20 ml of carbon dichloride solvent. Catalytic amount (0.1 g) of para-toluenesulfonic acid were added in solid phase to the solution, and the solution was agitated at room temperature for 1 hour. After washing the reaction mixture with water, organic solution parts were extracted with 30 ml of methylene chloride to gather them, and moisture was removed with anhydrous magnesium sulfate ($MgSO_4$). After filtering the solution, solvent was removed in a rotary evaporator, and the solution was dried under vacuum to obtain yellow solid compound.

The obtained compound was dissolved in 20 ml of n-hexane, and cooled at 20° C. overnight to obtain 1.76 g of ivory-colored solid compound $(C_5H_4)(C_6H_4)_2OH$ (yield 75%).

(Preparation of $(C_5H_4)C_6H_4)_2OTiCp*(OMe)_2$

The obtained $(C_5H_4)C_6H_4)_2OH$ was reacted with the same equivalent of $Cp*Ti(OMe)_2Cl$ by the same method as in Example 1 to obtain orange product $(C_5H_4)(C_6H_4)_2OTiCp*(OMe)_2$.

(Preparation of $(O^iPr)_3Ti[CP(C_6H_4)_2O]TiCp*(OMe)_2$ catalyst)

The synthesized $(C_5H_4)(C_6H_4)_2OTiCp*(OMe)_2$ was reacted with the same equivalent of $ClTi(OiPr)_3$ by the same method as in Example 1 to obtain $(O^iPr)_3Ti[Cp(C_6H_4)_2O]TiCp*(OMe)_2$.

Example 5

Synthesis of $(O^iPr)_3Ti[(C_5Me_4)(C_6H_4)_2O]TiCp*(OMe)_2$ $(O^iPr)_3Ti[(C_5Me_4)(C_6H_4)_2O]TiCp*(OMe)_2$ catalyst was prepared by the same method as in Example 4, except that 2,3,4,5-tetramethylcyclopent-2-enone is used instead of 2-cyclopenten-1-one.

Example 6

Synthesis of $(O^iPr)_3Ti[CpC_6H_4O]TiCp*(OMe)_2$ catalyst $(O^iPr)_3Ti[CpC_6H_4O]TiCp*(OMe)_2$ catalyst was prepared by the same method as in Example 4, except that $4\text{-}BrC_6H_4OH$ was used instead of $4\text{-}Br(C_6H_4)_2OH$.

Example 7

Synthesis of $(O^iPr)_3Ti[Cp(2,6\text{-}Me_2C_6H_2)O]TiCp*(OMe)_2$ catalyst $(O^iPr)_3Ti[Cp(2,6\text{-}Me_2C_6H_2)O]TiCp*(OMe)_2$ catalyst was prepared by the same method as in Example 4, except that $4\text{-}Br(2,6\text{-}Me_2C_6H_2)OH$ was used instead of $4\text{-}Br(C_6H_4)_2OH$.

Example 8

Synthesis of $(O^iPr)_3Ti[CpC_6H_4S]TiCp*(OMe)_2$ catalyst $(O^iPr)_3Ti[CpC_6H_4S]TiCp*(OMe)_2$ catalyst was prepared by the same method as in Example 4, except that $4\text{-}BrC_6H_4SH$ was used instead of $4Br(C_6H_4)_2OH$.

Example 9

Synthesis of $(O^iPr)_3Ti[CpC_6H_4CH_2O]TiCp*(OMe)_2$ catalyst $(O^iPr)_3Ti[CpC_6H_4CH_2O]TiCp*(OMe)_2$ catalyst was prepared by the same method as in Example 4, except that $4\text{-}BrC_6H_4CH_2OH$ was used instead of $4Br(C_6H_4)_2OH$.

Example 10

Preparation of Styrene Homopolymer (Liquid Phase Polymerization)

Liquid phase styrene homopolymerization was conducted using each of the multinuclear half metallocene catalysts synthesized in Examples 1 to 9.

To a polymerization reactor under high purity nitrogen atmosphere, 50 ml of purified heptane was added and temperature was elevated to 50° C. 50 ml of styrene, 2.5 ml (1.0 M) of triisobutylaluminum, and 2.5 ml of methylaluminoxane (2.1 M toluene solution, Akzo Company product) were sequentially introduced.

5 ml of toluene solution in which each of the metallocene catalysts was dissolved were added thereto, while vigorously agitating. After agitating for 30 minutes, 10 wt % of chloric acid-ethanol solution was added to terminate a reaction, and the reactant was filtered to obtain white solid precipitate. The precipitate was washed with ethanol and dried in a 50° C. vacuum oven overnight to obtain final styrene polymer. Results of polymerization and physical properties of polymers for each catalyst are shown in Table 1.

In addition, each of the polymers was refluxed in methylethylketone for 12 hours and extracted to obtain polymers that remain undissolved. As result of analyzing the polymers by carbon atom nuclear magnetic resonance spectroscopy, they were confirmed to have syndiotactic structure.

TABLE 1

Results of liquid phase styrene homopolymerization

| | Yield (g) | Activity (kgPS/ molTi · h) | Syndiotacticity (%) | Molecular weight ($\times 10^3$) | Molecular weight distribution | Melting point (° C.) |
|---|---|---|---|---|---|---|
| Catalyst of Example 1 $(O^iPr)_3Ti[Cp(CH_2)_6O]TiCp*(OMe)_2$ | 19.2 | 1456 | 92 | 205 | 14.5 | 269 |
| Catalyst of Example 2 $(O^iPr)_3Ti[Cp(CH_2)_9O]TiCp*(OMe)_2$ | 22.0 | 1760 | 93 | 220 | 15.6 | 270 |
| Catalyst of Example 3 $(O^iPr)_3Ti[Cp(CH_2)_{12}O]TiCp*(OMe)_2$ | 22.5 | 1800 | 93 | 225 | 15.2 | 270 |
| Catalyst of Example 4 $(O^iPr)_3Ti[Cp(C_6H_4)_2O]TiCp*(OMe)_2$ | 22.7 | 1816 | 94 | 240 | 16.8 | 271 |
| Catalyst of Example 5 $(O^iPr)_3Ti[(C_5Me_4)(C_6H_4)_2O]TiCp*(OMe)_2$ | 26.5 | 2120 | 97 | 310 | 11.5 | 272 |
| Catalyst of Example 6 $(O^iPr)_3Ti[CpC_6H_4O]TiCp*(OMe)_2$ | 20.3 | 1624 | 94 | 250 | 15.7 | 271 |
| Catalyst of Example 7 $(O^iPr)_3Ti[Cp(2,6\text{-}Me_2C_6H_2)O]TiCp*(OMe)_2$ | 21.1 | 1688 | 95 | 274 | 15.3 | 272 |
| Catalyst of Example 8 $(O^iPr)_3Ti[CpC_6H_4S]TiCp*(OMe)_2$ | 14.6 | 1168 | 93 | 210 | 17.8 | 269 |
| Catalyst of Example 9 $(O^iPr)_3Ti[CpC_6H_4CH_2O]TiCp*(OMe)_2$ | 19.8 | 1584 | 94 | 238 | 16.2 | 270 |

Example 11
Preparation of Styrene Homopolymer (Massive Phase Polymerization)

Massive phase styrene polymerization was conducted using the catalysts of Examples 3, 4, 5 and 7 having high liquid phase polymerization activity as that of Example 10 out of the multinuclear half metallocene catalysts synthesized in Examples 1 to 9.

To a polymerization reactor under high purity nitrogen atmosphere, 100 ml of purified styrene were added and temperature was elevated to 50° C. Then, 5 ml of triisobutylaluminum (1.0 M toluene solution) and 5 ml of methylaluminoxane (2.1 M toluene solution, Akzo Company product) were sequentially introduced therein.

5 ml (50 $\mu$mol of Ti) of toluene solution in which the metallocene is dissolved were added thereto while vigorously agitating. After agitating for 1 hour, 10 wt % of chloric acid-ethanol solution was added to terminate a reaction, and the reactant was filtered, washed with ethanol, and dried at a vacuum oven of 50° C. to obtain a final styrene polymer.

Results of polymerization and physical properties of polymers for each catalyst are shown in Table 2.

And, each polymer was refluxed in methylethylketone for 12 hours and extracted to obtain polymers that remained undissolved. As results of analyzing the polymers with carbon atom nuclear magnetic resonance spectroscopy, they were confirmed to have syndiotactic structures.

TABLE 2

|  | Yield (g) | Activity (kgPS/ molTi · h) | Syndiotacticity (%) | Molecular weight ($\times 10^3$) | Molecular weight distribution | Melting point (° C.) |
| --- | --- | --- | --- | --- | --- | --- |
| Catalyst of Example 3 $(O^iPr)_3Ti[Cp(CH_2)_{12}O]TiCp*(OMe)_2$ | 52.2 | 1044 | 91 | 280 | 21.5 | 268 |
| Catalyst of Example 4 $(O^iPr)_3Ti[Cp(C_6H_4)_2O]TiCp*(OMe)_2$ | 56.8 | 1136 | 92 | 340 | 18.4 | 270 |
| Catalyst of Example 5 $(O^iPr)_3Ti[(C_5Me_4)(C_6H_4)_2O]TiCp*(Ome)_2$ | 67.6 | 1352 | 94 | 478 | 15.9 | 271 |
| Catalyst of Example 6 $(O^iPr)_3Ti[Cp(2,6-Me_2C_6H_2)O]TiCp*)OMe)_2$ | 51.0 | 1020 | 92 | 325 | 19.6 | 270 |

Example 12
Preparation of Styrene/Ethylene Copolymer

Styrene/ethylene copolymerization was conducted using the catalysts of Examples 3, 4 and 5 having high styrene homopolymerization activity out of the multinuclear half metallocene catalyst of Examples 1 to 9.

To a polymerization reactor under high purity nitrogen atmosphere, 100 ml of purified styrene were added and temperature was elevated to 50° C. Then, 2 atm of ethylene was added to saturate, and 5 ml of triisobutylaluminum (1.0 M toluene solution) and 5 ml of methylaluminoxane (2.1 M toluene solution, Akzo company product) were sequentially introduced therein.

5 ml (50 $\mu$mol of Ti) of toluene solution in which the metallocene was dissolved were added thereto while vigorously agitating. After agitating for 2 hours, 10 wt % of chloric acid-ethanol solution was added to terminate a reaction and the reactant was filtered, washed with ethanol and dried in a vacuum oven of 50° C. to obtain a final styrene/ethylene copolymer.

Polymerization results and physical properties of polymers for each catalyst are shown in Table 3.

TABLE 3

| Results of styrene/ethylene copolymerization | | | | | |
| --- | --- | --- | --- | --- | --- |
|  | Yield (g) | Activity (kgPS/ molTi · h) | Ethylene contents (mol %) | Glass transition Temperature (° C.) | Melting point (° C.) |
| Catalyst of Example 3 $(O^iPr)_3Ti[Cp(CH_2)_{12}O]TiCp*(OMe)_2$ | 22.2 | 222 | 8.2 | 82 | 256 |
| Catalyst of Example 4 $(O^iPr)_3Ti[Cp(C_6H_4)_2O]TiCp*(OMe)_2$ | 21.5 | 215 | 10 | 80 | 240 |

TABLE 3-continued

Results of styrene/ethylene copolymerization

| | Yield (g) | Activity (kgPS/ molTi · h) | Ethylene contents (mol %) | Glass transition Temperature (° C.) | Melting point (° C.) |
|---|---|---|---|---|---|
| Catalyst of Example 5 (O$^i$Pr)$_3$Ti[(C$_5$Me$_4$)(C$_6$H$_4$)$_2$O]TiCp*(OMe)$_2$ | 18.6 | 186 | 6.4 | 93 | 260 |

Example 13

Preparation of Styrene/p-methylstyrene Copolymer

Styrene/p-methylstyrene copolymerization was conducted using catalyst of Examples 3, 4 and 5 having high styrene homopolymerization activity out of the multinuclear half metallocene catalyst of Examples of 1 to 9.

To a polymerization reactor under high purity nitrogen atmosphere, 100 ml of purified styrene and 5 ml of p-methylstyrene were added and temperature was elevated to 50° C. 5 ml of triisobutylaluminum (1.0 M toluene solution) and 5 ml of methylaluminoxane (2.1 M toluene solution, Akzo Company product) were sequentially introduced.

5 ml (50 μmol of Ti) of toluene solution in which the metallocene is dissolved were added while vigorously agitating. After agitating for 1 hour, 10 wt % of chloric acid-ethanol solution was added to terminate a reaction, the reactant was filtered, washed with ethanol and dried in a vacuum oven of 50° C. overnight to obtain a final styrene/p-methylstyrene copolymer.

Polymerization results and physical properties of polymers for each catalyst are shown in Table 4

TABLE 4

Results of styrene/p-methylstyrene copolymerization

| | Yield (g) | Activity (kgPS/ molTi · h) | p-methylstyrene contents (mol %) | Glass transition Temperature (° C.) | Melting point (° C.) |
|---|---|---|---|---|---|
| Catalyst of Example 3 (O$^i$Pr)$_3$Ti[Cp(CH$_2$)$_{12}$O]TiCp*(OMe)$_2$ | 50.5 | 1010 | 7.4 | 101 | 246 |
| Catalyst of Example 4 (O$^i$Pr)$_3$Ti[Cp(C$_6$H$_4$)$_2$O]TiCp*(OMe)$_2$ | 52.2 | 1044 | 8.0 | 100 | 244 |
| Catalyst of Example 5 (O$^i$Pr)$_3$Ti[(C$_5$Me$_4$)(C$_6$H$_4$)$_2$O]TiCp*(OMe)$_2$ | 64.8 | 1296 | 9.2 | 98 | 240 |

Example 14

Preparation of Styrene/1,3-butadiene Copolymer

Styrene/1,3-butadiene copolymerization was conducted using the catalyst of Examples 3, 4 and 4 having high styrene homopolymerization activity out of the multinuclear half metallocene catalysts of Examples 1 to 9.

To a polymerization reactor under high purity nitrogen atmosphere, 50 ml of purified styrene and 50 ml of 1,3-butadiene were added and reaction temperature was controlled to 25° C. Then, 5 ml of triisobutylaluminum (1,0 M toluene solution) and 5 ml of methylaluminoxane (2.1 M toluene solution, Akzo Company product) were sequentially introduced.

5 ml (50 μmol of Ti) of toluene solution in which the metallocene is dissolved was added while vigorously agitating. After agitating for 2 hours, 10 wt % of chloric acid-ethanol solution was added to terminate a reaction, the reactant was filtered, washed with ethanol and dried in a vacuum oven of 50° C. to obtain a final styrene/1,3-butadiene copolymer.

Polymerization results and physical properties of polymers for each catalyst are shown in Table 5

TABLE 5

|  | Yield (g) | Activity (kgPS/ molTi · h) | 1,3-butadiene contents (mol %) | Glass transition Temperature (° C.) | Melting point (° C.) |
| --- | --- | --- | --- | --- | --- |
| Catalyst of Example 3 $(O^iPr)_3Ti[Cp(CH_2)_{12}O]TiCp*(OMe)_2$ | 19.8 | 198 | 55 | 83 | 265 |
| Catalyst of Example 4 $(O^iPr)_3Ti(Cp(C_6H_4)_2O]TiCp*(OMe)_2$ | 21.2 | 212 | 41 | 84 | 267 |
| Catalyst of Example 5 $(O^iPr)_3Ti[(C_5Me_4)(C_6H_4)_2O]TiCp*(OMe)_2$ | 23.5 | 235 | 46 | 86 | 269 |

Comparative Example 1
Preparation Styrene Homopolymer Using $CpTi(OMe)_3$ and $Cp*Ti(OMe)_3$ Massive phase styrene homopolymerization was conducted by the same method as in Example 11, except that well known catalysts $CpTi(OMe)_3$ and $Cp*Ti(OMe)_3$ were used as a catalyst.

Polymerization results and physical properties of polymers for each catalyst are shown in Table 6

TABLE 6

Results of massive phase styrene homopolymerization using $CpTi(OME)_3$ and $Cp*Ti(OMe)_3$ as a catalyst

|  | Yield (g) | Activity (kgPS/ molTi · h) | Syndiotacticity (%) | Molecular weight (×10³) | Molecular weight distribution | Melting Point (° C.) |
| --- | --- | --- | --- | --- | --- | --- |
| CpTi(OMe)3 | 37.2 | 744 | 88 | 105 | 2.3 | 265 |
| Cp*Ti(OMe)3 | 64.0 | 1280 | 93 | 298 | 2.5 | 269 |

The group 3 to 10 transition metal multinuclear half metallocene catalyst of the present invention using a bridge ligand simultaneously containing π-ligand cycloalkandienyl group and σ-ligand functional group comprises a catalyst system with high activity together with a cocatalyst such as alkylaluminoxane, and syndiotactic styrene polymers and copolymers with olefins having superior stereoregularity, high melting temperature and various molecular weight distributions can be prepared therefrom. Polymers prepared according to the present invention have superior heat resistance, chemical resistance, drug resistance and processibility and thus can be variously applied for engineering plastics, etc.

What is claimed is:

1. A multinuclear half metallocene compound for preparing styrene polymer, represented by one of the following formulas:

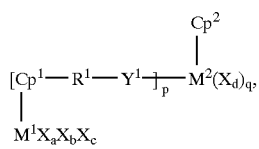

-continued

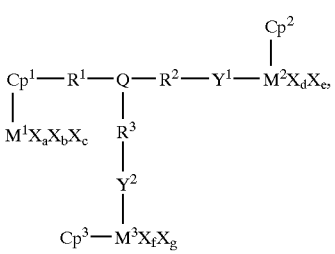

-continued

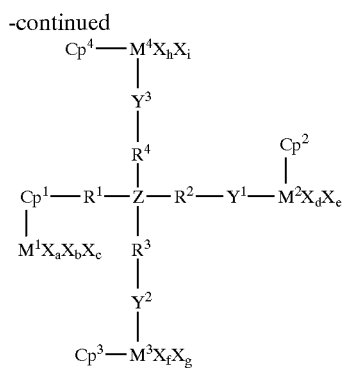

wherein,
$M^1$, $M^2$, $M^3$ and $M^4$ are, independently or simultaneously in the same formula, transition atoms of groups 3 to 10 on the periodic table;
$Cp^1$, $Cp^2$, $Cp^3$ and $Cp^4$ are, independently or simultaneously in the same formula, a cycloalkandienyl ligand represented by one of the following formulas:

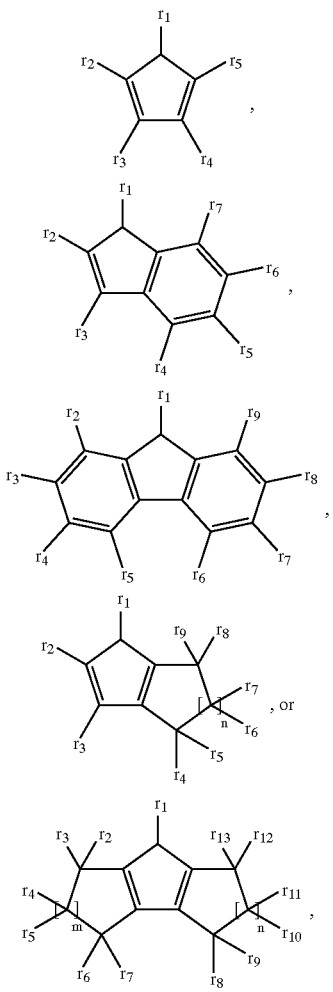

wherein, $r_1$, $r_2$, $r_3$, $r_4$, $r_5$, $r_6$, $r_7$, $r_8$, $r_9$, $r_{10}$, $r_{11}$, $r_{12}$ and $r_{13}$ are, independently or simultaneously in the same formula, hydrogen atom, halogen, C1–20 alkyl, cycloalkyl, alkenyl, alkylsilyl, haloalkyl, alkoxy, alkylsiloxy, amino, alkoxyalkyl, thioalkoxyalkyl, alkylsiloxyalkyl, aminoalkyl, alkylphosphinoalkyl, C6–40 aryl, arylalkyl, alkylaryl, arylsilyl, arylalkylsilyl, haloaryl, aryloxy, aryloxoalkyl, thioaryloxoalkyl, aryloxoaryl, arylsiloxy, arylalkylsiloxy, arylsiloxalkyl, arylsiloxoaryl, arylamino, arylaminoalkyl, arylaminoaryl or arylphosphinoalkyl group; and
each of m and n is an integer of 1 or more;

$X_a$, $X_b$, $X_c$, $X_d$, $X_e$, $X_f$, $X_g$, $X_h$ and $X_i$, which are σ-ligand functional groups, are independently or simultaneously in the same formula, hydrogen atom, halogen, hydroxy, C1–20 alkyl, cycloalkyl, alkylsilyl, alkenyl, alkoxy, alkenyloxy thioalkoxy, alkylsiloxy, amide, alkoxyalcohol, alcoholamine, carboxyl, sulfonyl, C6–40 aryl, alkylaryl, arylalkyl, arylsilyl, haloaryl, aryloxy, arylalkoxy, thioaryloxy, arylsiloxy, arylalkylsiloxy, arylamide, arylalkylamide, aryloxoalcohol, alcohoarylamine, or arylaminoaryloxy group;

$R^1$, $R^2$, $R^3$ and $R^4$, which are bridging groups connecting the transition metal $M^1$, $M^2$, $M^3$ or $M^4$ with the cycloalkandienyl ligand $Cp^1$, $Cp^2$, $Cp^3$ or $Cp^4$, are independently or simultaneously in the same formula, C1–20 alkyl, cycloalkyl, alkenyl, alkylsilyl, haloalkyl, alkoxy, alkylsiloxy, amino, dialkylether, dialkylthioether, alkylsiloxyalkyl, alkylaminoalkyl, alkylphosphinoalkyl, C6–40 aryl, arylalkyl, alkylaryl, arylsilyl, arylalkylsilyl, haloaryl, aryloxy, aryloxoalkyl, thioaryloxoalkyl, aryloxoaryl, arylsiloxy, arylalkylsiloxy, arylsiloxoalkyl, arylsiloxoaryl, arylamino, arylaminoalkyl, arylaminoaryl or arylphosphinoalkyl group;

Z is a carbon, silicon or germanium;

Q is a nitrogen, phosphorous, C-$r_{14}$, Si-$r_{15}$ or Ge-$r_{16}$;

$Y^1$, $Y^2$ and $Y^3$, which are σ-ligand functional groups, are independently or simultaneously in the same formula, oxygen, sulfur, carboxylic group, sulfonyl group, N-$r_{17}$ or P-$r_{18}$; wherein, in the C-$r_{14}$, Si-$r_{15}$, Ge-$r_{16}$, N-$r_{17}$ and P-$r_{18}$, each of $r_{14}$, $r_{15}$, $r_{16}$, $r_{17}$ and $r_{18}$ is selected from a group consisting of hydrogen, halogen, C1–20 alkyl, cycloalkyl,1 alkenyl, alkylsilyl, haloalkyl, alkoxy, alkylsiloxy, amino, alkoxyalkyl, thioalkoxyalkyl, alkylsiloxyalkyl, aminoalkyl, alkylphosphinoalkyl, aryl, arylalkyl, alkylaryl, arylsilyl, arylalkylsilyl, haloaryl, aryloxy, aryloxoalkyl, thioaryloxoalkyl, aryloxoaryl, arylsiloxy, arylalkylsiloxy, arylsiloxoalkyl, arylsiloxoaryl arylamino, arylaminoalkyl, arylaminoaryl and arylphosphinoalkyl group; and p is an integer of 1 to 3, q is an integer of 0 to 2, and p+q=3.

2. A process for preparing styrene polymer comprising polymerizing styrene monomers in the presence of a catalyst system, wherein the catalyst system comprises:

a cocatalyst selected from a group consisting of
  alkylaluminoxane;
  a mixture of alkylaluminoxane and alkylaluminum; and
  a mixture of weak coordinate Lewis acid and alkylaluminum; and a multinuclear half metallocene compound catalyst represented by one of the following formulas:

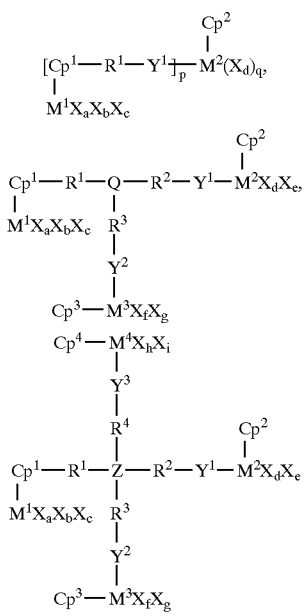

wherein,

M¹, M², M³ and M⁴ are, independently or simultaneously in the same formula, transition atoms of groups 3 to 10 on the periodic table;

Cp¹, Cp², Cp³ and Cp⁴ are, independently or simultaneously in the same formula, cycloalkandienyl ligand represented by one of the following formulas:

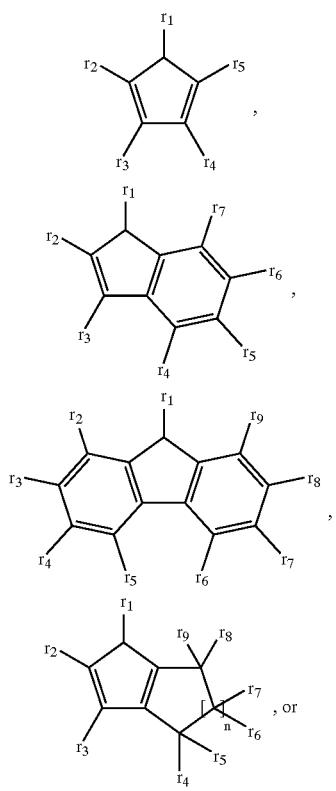

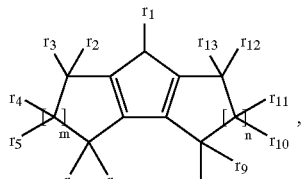

wherein, $r_1, r_2, r_3, r_4, r_5, r_6, r_7, r_8 r_9, r_{10}, r_{11}, r_{12}$ and $r_{13}$ are, independently or simultaneously in the same formula, hydrogen atom, halogen, C1–20 alkyl, cycloalkyl, alkenyl, alkylsilyl, haloalkyl, alkoxy, alkylsiloxy, amino, alkoxyalkyl, thioalkoxyalkyl, alkylsiloxyalkyl, aminoalkyl, alkylphosphinoalkyl, C6–40 aryl, arylalkyl, alkylaryl, arylsilyl, arylalkylsilyl, haloaryl, aryloxy, aryloxoalkyl, thioaryloxoalkyl, aryloxoaryl, arylsiloxy, arylalkylsiloxy, arylsiloxalkyl, arylsiloxoaryl, arylamino, arylaminoalkyl, arylaminoaryl or arylphosphinoalkyl group; and each of m and n is an integer of 1 or more;

$X_a, X_b, X_c, X_d, X_e, X_f, X_g, X_h$ and $X_i$, which are σ-ligand functional groups, are independently or simultaneously in the same formula, hydrogen atom, halogen, hydroxy, C1–20 alkyl, cycloalkyl, alkylsilyl, alkenyl, alkoxy, alkenyloxy, thioalkoxy, alkylsiloxy, amide, alkoxyalcohol, alcoholamine, carboxyl, sulfonyl, C6–40 aryl, alkylaryl, arylalkyl, arylsilyl, haloaryl, aryloxy, arylalkoxy, thioaryloxy, arylsiloxy, arylalkylsiloxy, arylamide, arylalkylamide, aryloxoalcohol, alcohoarylamine, or arylaminoaryloxy group;

R¹, R², R³ and R⁴, which are bridging groups connecting the transition metal M¹, M², M³ or M⁴ with the cycloalkandienyl ligand Cp¹, Cp², Cp³ or Cp⁴, are independently or simultaneously in the same formula, C1–20 alkyl, cycloalkyl, alkenyl, alkylsilyl, haloalkyl, alkoxy, alkylsiloxy, amino, dialkylether, dialkylthioether, alkylsiloxyalkyl, alkylaminoalkyl, alkylphosphinoalkyl C6–40 aryl, arylalkyl, alkylaryl, arylsilyl, arylalkylsilyl, haloaryl, aryloxy, aryloxoalkyl, thioaryloxoalkyl, aryloxoaryl, arylsiloxy, arylalkylsiloxy, arylsiloxoalkyl, arylsiloxoaryl, arylamino, arylaminoalkyl, arylaminoaryl or arylphosphinoalkyl group;

Z is carbon, silicon or germanium;

Q is nitrogen, phosphorous, C-$r_{14}$, Si-$r_{15}$ or Ge-$r_{16}$;

Y¹, Y² and Y³, which are σ-ligand functional groups, are independently or simultaneously in the same formula, oxygen, sulfur, carboxylic group, sulfonyl group, N-$r_{17}$, or P-$r_{18}$; wherein, in the C-$r_{14}$, Si-$r_{15}$, Ge-$r_{16}$, N-$r_{17}$ and P-$r_{18}$, each of $r_{14}, r_{15}, r_{16}, r_{17}$ and $r_{18}$ is selected from a group consisting of hydrogen, halogen, C1–20 alkyl, cycloalkyl, alkenyl, alkylsilyl, haloalkyl, alkoxy, alkylsiloxy, amino, alkoxyalkyl, thioalkoxyalkyl, alkylsiloxyalkyl, aminoalkyl, alkylphosphinoalkyl, aryl, arylalkyl, alkylaryl, arylsilyl, arylalkylsilyl, haloaryl, aryloxy, aryloxoalkyl, thioaryloxoalkyl, aryloxoaryl, arylsiloxy, arylalkylsiloxy, arylsiloxoalkyl, arylsiloxoaryl, arylamino, arylaminoalkyl, arylaminoaryl and arylphosphinoalkyl group; and p is an integer of 1 to 3, q is an integer of 0 to 2, and p+q=3.

3. The process for preparing styrene polymer according to claim 2, wherein the styrene monomers are styrene, styrene derivatives, a mixture of styrene and its derivatives, a mixture of styrene and olefin, or a mixture of styrene derivatives and olefin.

4. The process for preparing styrene polymer according to claim 2, wherein the polymerization product is styrene homopolymer, styrene derivative homopolymer, copolymer of styrene and its derivative, copolymer of styrene and olefin, or copolymer of styrene derivative and olefin.

* * * * *